US006955170B1

(12) United States Patent
Mullins et al.

(10) Patent No.: US 6,955,170 B1
(45) Date of Patent: Oct. 18, 2005

(54) AUTOMATED RESPIRATOR FIT TESTING METHOD AND SYSTEM

(75) Inventors: Haskell E. Mullins, Cottage Grove, MN (US); Paul A. Martinson, Maplewood, MN (US); Alan R. Johnston, West St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 464 days.

(21) Appl. No.: 09/698,412

(22) Filed: Oct. 27, 2000

(51) Int. Cl.[7] .................... A61M 15/00; A61M 16/00; A61M 18/00; A61M 7/00; A61M 9/00

(52) U.S. Cl. .......................... 128/200.24; 128/200.14; 128/202.22; 128/205.23; 128/206.24; 73/40

(58) Field of Search .................... 128/200.14, 201.23, 128/200.24, 202.22, 203.21, 205.23, 206.14, 128/206.24; 73/38, 40; 424/74.3

(56) References Cited

U.S. PATENT DOCUMENTS

| | | | | |
|---|---|---|---|---|
| 2,420,372 A * | 5/1947 | Heidbrink | 73/40 |
| 3,580,051 A * | 5/1971 | Blevins | 73/40 |
| 4,146,025 A * | 3/1979 | Warncke et al. | 128/200.24 |
| 4,846,166 A | 7/1989 | Willeke | |
| 4,914,957 A * | 4/1990 | Dougherty | 73/40 |
| 5,156,776 A * | 10/1992 | Loedding et al. | 261/27 |
| 5,233,975 A * | 8/1993 | Choate | 128/200.14 |
| 5,289,819 A * | 3/1994 | Kroger et al. | 128/200.24 |
| 5,320,108 A * | 6/1994 | Cloutier | 128/203.25 |
| 5,500,027 A * | 3/1996 | Rudolph et al. | 55/223 |
| 5,529,056 A * | 6/1996 | Brunson et al. | 128/200.24 |
| 5,584,125 A | 12/1996 | Prete | |
| 5,647,356 A | 7/1997 | Osendorf et al. | |
| D389,910 S | 1/1998 | Brunson et al. | |
| 5,752,054 A | 5/1998 | Garber et al. | |
| 5,893,070 A | 4/1999 | Garber et al. | |
| 5,963,743 A | 10/1999 | Amberg et al. | |
| 6,125,845 A * | 10/2000 | Halvorsen et al. | 128/200.24 |
| 6,435,009 B1 * | 8/2002 | Tilley | 73/40 |

FOREIGN PATENT DOCUMENTS

DE 2652136 3/1979

(Continued)

OTHER PUBLICATIONS

DA Pam 40-8 Occupational Health Guidelines for Eval. & Control of Occupational Exposure, Dec. 4, 1990.*

(Continued)

*Primary Examiner*—Henry Bennett
*Assistant Examiner*—Amanda Wieker
(74) *Attorney, Agent, or Firm*—Kevin W. Raasch; Karl G. Hanson

(57) ABSTRACT

A system and method for the remote administration of respirator fit tests are disclosed, along with a system and method for administering qualitative respirator fit tests to two or more test subjects simultaneously. Remote administration of respirator fit tests involves the testing of test subjects located at one facility by a test administrator located at a different facility. The two facilities may be located, for example, in the same city, in different countries, etc. As a result, a single test administrator may, for example, be able to administrate fit tests with test subjects located in a variety of facilities in one day without traveling. Qualitative respirator fit testing systems and methods of the invention include multiple test stations and an aerosol generator system in fluid communication with each of the test stations. The aerosol generator system may be capable of delivering aerosol to the test stations in repeatable, selected amounts and may also be capable of delivering the aerosols to some or all of the stations simultaneously.

39 Claims, 2 Drawing Sheets

FOREIGN PATENT DOCUMENTS

| | | | | |
|---|---|---|---|---|
| FR | 724174 | * | 4/1932 | ............ 128/200.24 |
| GB | 1546550 | | 5/1979 | |

OTHER PUBLICATIONS

Prototype Test Chamber for Fit Testing of Protective Masks in the field, FOA Report C40208-C1(C2) Dec. 1984 Burstroem.*

Department of the Army, Pamphlet 40-8. "Occupational Health Guidelines for the Evaluation and Control of Occupational Exposure to Nerve Agents GA, GB, GD and VX", Dec. 4, 1990.*

OSHA Standards Interpretation and Compliance Letters Aug. 27, 1999—Appendix A requirements and techniques for fit testing respirators. Regulations [online]. 2 pgs. Occupational Safety & Health Administration, U.S. Department of Labor, 1999 [retrieved on Aug. 29, 2000]. Retrieved from the Internet: <URL: http://www/osha-slc.gov/OshDoc/Interp_data/119990827.html>.

PORTACOUNT® Plus Respirator Fit Tester Features, Specifications, and Accessories Revised Dec. 23, 1998. Datasheet [online]. 4 pgs. TSI Incorporated, 1996 [retrieved on Apr. 6, 2000]. Retrieved from the Internet: <URL: http://www.tsi.com/hsi/homepage/portcont/portspec.htm>.

TDA-99M Protective Mask Leakage Tester. Datasheet [online]. 3 pgs. Air Techniques International, 1998 [retrieved on Apr. 6, 2000]. Retrieved from the Internet: <URL: http://www.atitest.com/pages/TDA99M.htm>.

DUSTTRAK™ Aersol Monitor Model 8520 Features, Specifications, and Accessories Revised Feb. 16, 2000. Datasheet [online]. 4 pgs. TSI Incorporated, 1997 [retrieved on Apr. 6, 2000]. Retrieved from the Internet: <URL: http://www.tsi.com/hsi/homepage/dusttrak/dustspec.htm>.

N95-COMPANION™ Features, Specifications, and Accessories Revised Dec. 23, 1999. Datasheet [online]. 4 pgs. TSI Incorporated, 1997 [retrieved on Apr. 6, 2000]. Retrieved from the Internet: <URL: http://www.tsi.com/hsi/homepage/n95/n95_spec.htm>.

OSHA Regulations (Standards—29 CFR) Fit Testing Procedures (Mandatory).-1910.134 App A. Regulations [online]. 17 pgs. Occupational Safety & Health Administration, U.S. Department of Labor, 1998 [retrieved on Aug. 29, 2000]. Retrieved from the Internet: <URL: http://www.osha-slc.gov/OshStd_data/1910_0134_APP_A.html>.

K.P. Fennelly et al., "An Automated Aerosol Generator to Reduce Variability in Qualitative Fit Testing of Respirators," American Journal of Respiratory and Critical Care Medicine, vol. 159, Supplement #3, pp. A615 (1 pg) (1999).

Burström et al., "Prototype Test Chamber For Fit Testing of Protective Masks in the Field," Swedish National Defense Research Institute (SNDRI), 21 pgs total (Dec. 1984).

English translation of Burström et al., "Prototype Test Chamber For Fit Testing of Protective Masks in the Field," Swedish National Defense Research Institute (SNDRI), (Dec. 1984) (7 pgs).

* cited by examiner

AUTOMATED RESPIRATOR FIT TESTING METHOD AND SYSTEM

The present invention relates to an automated respirator fit testing method and system.

BACKGROUND

Respirators are worn over at least the mouth and nose of a person for two common purposes: (1) to prevent impurities or contaminants from entering the wearer's breathing tract; and/or (2) to protect others from being exposed to pathogens and other contaminants exhaled by the wearer. In the first situation, the respirator is worn in an environment where the air contains particles harmful to the wearer, for example, in an auto body shop. In the second situation, the respirator is worn in an environment where there is a high risk of infection, for example, in an operating room. To accomplish either of these purposes, a snug fit to the wearer's face must be maintained.

Respirators are commonly fit tested to determine whether they have the proper size or shape and whether they can be can be adjusted to provide an adequate seal between the respirators and the wearers' faces. Respirator fit testing has been required by various government agencies. In the United States, respirator fit testing is regulated according to 29 C.F.R. § 1910.134 (Appendix A). The regulations vary depending on the type of test being performed, for example, whether the removal efficiency of the respirator is 95%, 99%, or 99.97%.

Qualitative respirator fit testing typically involves a one-on-one test conducted by a trained test administrator on a test subject. The test subject dons a respirator and, within a controlled environment, is exposed to an aerosol that can be detected by taste or odor. The aerosols that are used in taste response testing are generated manually by a test administrator using a squeeze bulb attached to a nebulizer. The test typically involves having the test subject perform a variety of exercises, such as deep breathing, head rotation, etc., to assess the viability of the seal under conditions that may be encountered by the test subject.

Variability in respirator test results is one disadvantage of qualitative respirator fit testing. For example, the aerosol concentration levels to which the test subjects are exposed may vary if the test administrators do not manually deliver the same amount of test aerosol. Other fit testing variations may be found in the content and/or timing of prompts provided to the test subjects when directing them to perform activities as a part of the fit testing procedure.

Other disadvantages of known respirator fit testing procedures may include the cost and/or limited availability of trained personnel to carry out the tests for all of the individuals requiring them. In some instances, fit testing may be required in locations that are far removed from the location of trained test administrators. This can require travel by the test administrator or the personnel requiring fit testing to complete the required tests.

SUMMARY OF THE INVENTION

The present invention addresses a number of the problems that are associated with qualitative respirator fit testing by, in one aspect, providing an automated system and method for the remote administration of qualitative respirator fit tests. In another aspect, the present invention addresses the problems associated with qualitative respirator fit testing by providing a system and method for administering qualitative respirator fit tests to two or more test subjects simultaneously.

Among the methods of the present invention, remote administration of qualitative respirator fit tests involves the testing of test subjects located at one facility by a test administrator located at a different facility. The two facilities may be located, for example, in the same city, in different countries, etc. As a result, a single test administrator may, for example, be able to administrate fit tests with test subjects located in a variety of facilities in one day without traveling. As a further advantage, the same test administrator may be able to conduct fit tests at two or more locations at the same time.

In other variations, the present invention provides an automated qualitative respirator fit testing system and method that is capable of testing two or more individuals at the same time. The system includes multiple test stations and an automated aerosol generator system in fluid communication with each of the test stations. The automated aerosol generator system may be capable of delivering aerosol to the test stations in repeatable, selected amounts and may also be capable of delivering the aerosols to some or all of the stations simultaneously.

Among the advantages of the present invention are an increase in the availability of qualitative respirator fit tests and a corresponding potential decrease in the cost of administering each test. Providing a test administrator with a fit test system including an automated aerosol generator system in fluid communication with multiple test stations enables fit testing of two or more test subjects at the same time using a single fit testing system. As a result, the number of tests conducted by the test administrator may increase and the cost of administering the fit tests may, correspondingly, decrease.

Another advantage of the present invention is the reduction of at least some of the variability in qualitative respirator fit tests. For example, the use of an automated aerosol generator system reduces or eliminates the variability that may be encountered with the use of manual squeeze-bulbs. In addition, in those methods in which the activity prompts are automatically delivered from, e.g., a computerized device, variability in the content and/or timing of prompts provided to test subjects during respirator fit testing can also be reduced or eliminated.

In one aspect, the present invention provides a method of qualitative respirator fit testing that includes providing an automated qualitative respirator fit testing system with a plurality of test stations and an automated aerosol generator system in fluid communication with each of the test stations. The method also includes locating at least one test subject at one test station of the plurality of test stations and conducting a qualitative fit test on each test subject located at one of the test stations. The qualitative fit test includes delivering a test aerosol to the test station using the automated aerosol generator system after locating a respirator on the test subject, wherein the test subject is exposed to the test aerosol, and receiving test feedback from the test subject at the test station after exposure to the test aerosol. In one alternative, the method may involve locating at least two test subjects at the plurality of test stations and simultaneously conducting two qualitative fit tests on each of the at least two subjects located at the test stations.

In another aspect, the present invention provides a qualitative respirator fit testing system that includes a plurality of test stations and an automated aerosol generator system in fluid communication with each of the test stations. The automated aerosol generator system may include a set of independent aerosol generators, wherein at least one of the independent aerosol generators is in fluid communication with each of the test stations. Alternatively, the automated aerosol generator system may include at least one aerosol generator in fluid communication with at least two of the plurality of test stations.

In another aspect, the present invention provides a method of remote respirator fit testing that includes providing an automated respirator fit testing system at a first location, wherein the respirator fit testing system has at least one test station and an automated aerosol generator system in fluid communication with each of the at least one test stations. At least one test subject wearing a respirator is located at the test station. The respirator fit testing system is operated from a remote location to perform a respirator fit test on the test subject by delivering a test aerosol to the test station using the automated aerosol generator system, wherein the at least one test subject is exposed to the test aerosol.

These and other features and advantages of the invention may be described in more detail below with reference to various illustrative embodiments of the invention.

GLOSSARY

In reference to the invention, the following terms are defined as set forth below. Other terms may also be explicitly defined in the detailed description or with reference to the specification, claims and drawings.

"Aerosol" means a gas that contains suspended particles in solid and/or liquid form;

"automated aerosol generator system" means an aerosol generator system that generates aerosols without the use of manual squeeze bulbs;

"monitoring" (and variations thereof) means visual observation by a person or machine-based monitoring by a camera or similar device;

"qualitative respirator fit test" (and variations thereof) means a respirator fit test that relies on the taste and/or smell response of the test subject to detect leakage of a respirator; and "respirator" means a system or device worn over a person's breathing passages to prevent contaminants from entering the wearer's respiratory tract and/or to protect other persons or things from exposure to pathogens or other contaminants expelled by the wearer during respiration, including, but not limited to filtering face masks.

DETAILED DESCRIPTION OF ILLUSTRATIVE EMBODIMENTS OF THE INVENTION

Figure 1:
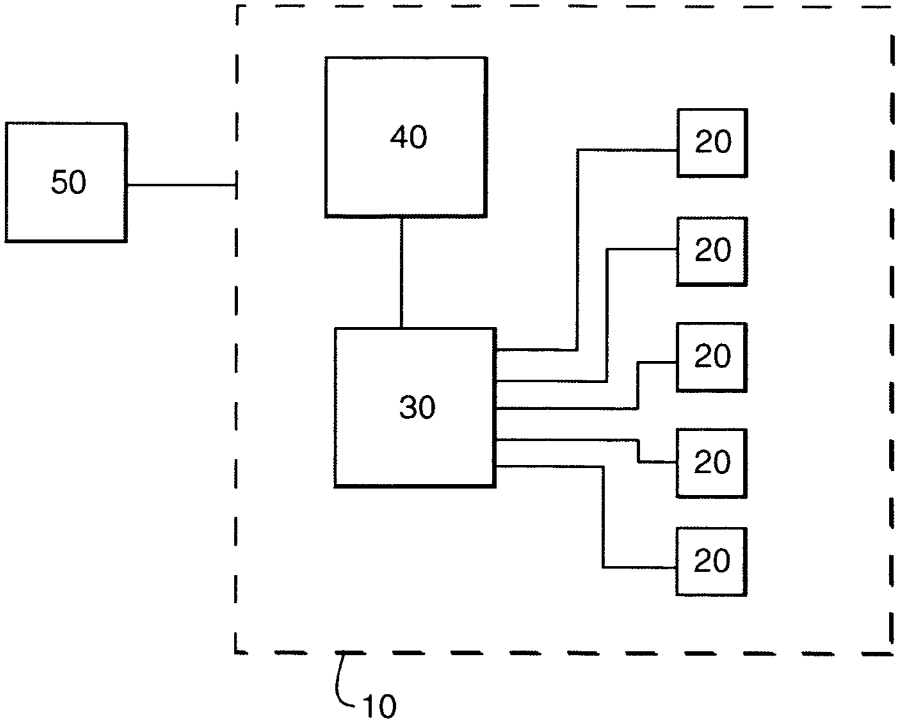
FIG. 1 is a schematic diagram of one test administrator 50 using a fit testing system 10 including multiple test stations 20, an automated aerosol generator system 30, and a controller 40.

FIG. 1 is a schematic diagram of one qualitative respirator fit testing system 10 under the control of a test administrator 50. The fit testing system 10 includes multiple test stations 20 connected to an automated aerosol generator system 30. The aerosol generator system 30 is controlled by a controller 40 that, in the illustrated embodiment, is operated by the test administrator 50.

The controller 40 may be provided in any suitable form, e.g., a hardwired control device or a data processing system, e.g., a personal computer or workstation that includes a processor, one or more display devices, one or more input devices, one or more data storage devices, and one or more printers or other output devices. In some instances, the controller may include a combination of one or more hardwired control devices and one or more data processing systems.

The test aerosols generated during qualitative fit testing rely on taste and/or smell response of the test subject for detection. Potential aerosols for qualitative fit testing may include, but are not limited to, isoamyl acetate, saccharin, denatonium benzoate (available under the tradename BITREX from Mcfarlan Smith Company, Edinburgh, UK), stannic chloride, etc. One exemplary test aerosol source solution for use in a Class 95 fit testing protocol (where 95% removal efficiency is required) may be a mixture of 5% bw BITREX in saline solution (using BITREX with a concentration of 1.6875 mg/ml). The same BITREX material can be used to provide a sensitivity aerosol source solution, although the BITREX used is at a concentration of 0.135 mg/ml (again mixed with saline at a 5% bw).

Although the fit testing system 10 is depicted with five test stations 20, fit testing systems 10 of the present invention may include as few as two test stations 20 or more that five test stations 20 and the depiction of system 10 with five stations should not be construed as limiting to the invention. During fit testing, the test stations 20 each provide an independent environment in which a test subject is exposed to a test aerosol delivered by the automated aerosol generator system 30. By "independent environment," it is meant that the test aerosol delivered to one of the test stations 20 cannot be communicated to another of the test stations 20. As a result, fit tests can be conducted simultaneously, but independently, at two or more of the test stations 20.

Each test station 20 will typically include some structure that defines an enclosed volume in which the nose and mouth of a test subject can be located. For example, the test stations 20 may be provided in the form of a room or booth in which the test subject may be located. Alternatively, it may be necessary only to provide a testing hood that fits over, e.g., the test subject's head. Such testing hoods are commonly used in connection with respirator fit testing because of their convenience.

The automated aerosol generator system 30 depicted in connection with fit testing system 10 includes a central aerosol generator in fluid communication with each of the test stations 20 as depicted in FIG. 1. By "fluid communication" as used herein, it is meant that the central aerosol generator system 30 is capable of delivering aerosol to the test stations 20. In the configuration depicted in FIG. 1, the central aerosol generator 30 may be in fluid communication with the test stations 20 by fluid conduits, even though those fluid conduits may be closed at any given time by, e.g., valves or other mechanisms. It may be preferred, but not required, that the central aerosol generator system 30 be capable of delivering an aerosol to two or more of the test stations 20 at the same time.

Also a part of the qualitative fit testing system 10 illustrated in FIG. 1 is a controller 40. The controller 40 is depicted as being in communication with the aerosol generator system 30 as well as with each of the fit testing stations 20. The controller 40 preferably provides operating control over the functions of the aerosol generator system 30, determining such activities as the amounts and times at which the various aerosols used in the fit tests are delivered to each test station 20. The automated aerosol generator system 30 and controller 40 can be located remote from each other and connected by any suitable technique, e.g., modem, hardwire connection, radio control, computer network connection, etc. Further, although the controller 40 is depicted as separate from the aerosol generator system 30, the controller 40 and aerosol generator system 30 could be integrated into a single unit, if so desired.

The controller 40 may also optionally be connected to each of the test stations 20. The connections between the controller 40 and the test stations 20 may be provided for a number of reasons. In some embodiments, the controller 40 may be connected to each of the test stations 20 to receive feedback from the test subjects during the fit testing process. That feedback to the controller 40 may be provided in any suitable manner, e.g., by voice, action by the test subject (such as pressing a button, keyboard, nodding, blinking, etc.), inaction by the test subject, etc. The feedback may be indicative of a number of things, e.g., detection of an aerosol by the test subject, completion of an activity by a test subject, selection of one option from a list of potential choices, etc.

In other embodiments, the controller 40 may be connected to the test stations 20 for a number of other reasons. For example, the controller 40 may provide prompts to the test subjects requesting that they perform certain activities, provide them with information regarding the fit testing process, request that they select a language for conducting the fit test, etc. The prompts may be visible and/or audible to the test subject.

In other cases, the controller 40 may be connected to a monitoring device located at the test station 20 to monitor the test subject during fit testing. The monitoring may be performed by cameras, or it may involve monitoring other physiological responses such as the test subject's pulse, breathing, etc. If performed by cameras, the image or images generated may be captured and stored at the controller 40 or in some other place or device for reference purposes.

The controller 40 may also be connected to one or more devices within the test stations 20 that detect aerosol concentration levels, humidity, temperature, flow rate, etc.

The test administrator 50 is an optional feature of the methods of the present invention. In some instances, the fit testing process may be completed in the absence of test administrator 50 if the fit testing system 10 is capable of providing the prompts required to complete the fit testing process and receive and store the feedback generated by the test subjects during the tests. The presence of a fit test administrator 50 may, however, be helpful if the fit testing system, for example, lacks the capabilities to operate as a stand-alone device. In other instances, it may be preferred to have someone present at the test location directing and/or monitoring testing to increase the comfort level of the test subjects, insure compliance with test protocols, monitor the equipment for malfunctions, etc. That person may or may not, however, be a trained test administrator. For example, a person may be present merely to attend to the equipment, if necessary.

Due to the nature of the fit testing system 10, however, it may not be necessary for the test administrator 50 to be physically present in the proximity of the test stations 20. Because the automated aerosol generator system 30 is used to provide the aerosols used during the fit testing, the test administrator 50 may be located at a remote site and be in communication with the test stations 20 through, e.g., a voice link, voice and video link, text link, etc.

If a test administrator 50 is used to administer the fit tests, the controller 40 may not need to be connected to the test stations 20 as depicted in FIG. 1. Rather, the controller may only operate the aerosol generator system 30 while the test administrator 50 provides the prompts to and receives feedback from the test subjects at the test stations 20. It may, however, be preferred that the controller 40 issue the prompts to and/or receive feedback from the test subjects to allow the test administrator 50 to address unexpected issues that may be encountered during fit testing.

According to one version of the methods of the present invention, at least one test subject is positioned at one of the test stations 20 of a qualitative fit testing system 10 that includes multiple fit testing stations 20 in fluid communication with an automated aerosol generator system 30. A qualitative fit test conducted at test station 20 includes delivering a test aerosol using the aerosol delivery system 30, thereby exposing the test subject at the station 20 to the test aerosol (after the test subject has donned the respirator to be tested). After exposure, test feedback is received from the test subject, indicating, for example, detection or no detection of the test aerosol by the test subject.

Although the methods of the invention may include testing a single test subject using a fit testing system that includes multiple test stations, it may be preferred that two or more test subjects be positioned at test stations 20. Fit tests can then be conducted simultaneously on at least two of the test subjects at the test stations 20. Although the fit tests are conducted simultaneously, it is not necessarily required that each of the fit tests be performed in complete synchronicity. In other words, the fit tests on the different tests subjects may progress at different rates, so long as at least two test subjects are engaged in fit testing by the fit testing system 10 at the same time.

One additional optional feature of methods of the present invention may include, for example, storing the test feedback in a database. That database may, optionally, include personal identification information regarding the test subject being fit tested. In the case of test feedback, that test feedback information may be correlated with the personal identification information of the test subject.

Other additional optional features of the methods of the present invention may include monitoring each of the test stations 20 during exposure of the test subjects at those stations 20 to the test aerosol. As discussed above, that monitoring may be accomplished in a variety of manners. It may be preferred, however, that the monitoring involve real-time visual monitoring by a test administrator 50 during administration of the tests (e.g., in personal, by video link between remote locations, etc.). Visual monitoring may alternatively be accomplished by capturing images of the test subjects during fit testing using, e.g., cameras or similar devices. If one or more images are captured during monitoring of the test stations 20, the captured image or images may also be stored in the database, preferably correlated to the personal identification information of the appropriate test subject for future reference. It may be preferred that both real-time visual monitoring by a test administrator 50 and visual monitoring by the capture of images be performed in connection with the present invention.

As a part of the methods of the present invention, it may be preferred that the automated aerosol generator system 30 deliver selected amounts of the test aerosol to each of the test stations 20 occupied by a test subject at predetermined intervals during at least a portion of the fit testing. The delivery of selected amounts of test aerosol at predetermined time intervals may be useful for establishing and maintaining a desired concentration level of the test aerosol at each test station 20.

Delivery of test aerosol to the test stations 20 by the automated aerosol generator system 30 may also involve simultaneous delivery of test aerosol to at least two of the test stations 20. Alternatively, the test aerosol may not be delivered simultaneously.

Other variations in the methods and systems of the invention may include the delivery of different selected amounts of the test aerosol to different test stations 20 or the delivery of the same selected amount of test aerosol to different test stations 20 at different time intervals. These variations in the basic method may be used to accommodate simultaneous fit testing of test subjects at different test stations 20 that exhibit different levels of aerosol sensitivity. Those different sensitivity levels may require exposure of the different test subjects to different concentrations of the test aerosol during the fit testing process. Changing the amount of test aerosol delivered by the automated aerosol generator system 30 and/or the time intervals at which those amounts are delivered may accommodate those differences.

The fit testing methods may also optionally involve prompting the test subjects at the test stations 20 to perform specified activities during exposure to the test aerosol. Those activities may include, for example, normal breathing, deep breathing, side-to-side head movement, up-and-down head movement, talking, bending at the torso, jogging in place, etc. The prompting may be provided by a test administrator 50 (if present) or by the system 10 itself (e.g., from controller 40). Prompting may be simultaneously provided to at least two or more of the test subjects at the test stations 20. Alternatively, the prompting may not be provided simultaneously.

The fit testing methods of the present invention may also optionally include receiving activity feedback from each of the test subjects. The activity feedback may, for example, be indicative of the completion of one or more of the specified activities. This activity feedback may be helpful for those fit testing systems 10 in which the different test subjects at the different test stations can proceed through the fit testing process at different rates. For example, the controller 40 and/or test administrator 50 may wait to receive an indication from the test subject that a prompted specified activity is complete before prompting that test subject to perform a different specified activity. The activity feedback may also be stored in the database where it is preferably correlated with the personal identification information of the test subject providing the activity feedback.

In many qualitative fit testing processes, it may be necessary to establish the taste and/or smell response sensitivity of each test subject to aerosols. Different sensitivity levels may require exposure of that individual to different concentration levels of the test aerosol or aerosols. In connection with the present invention, the sensitivity of each test subject may be established using systems and/or methods that do not fall within the scope of the present invention. For example, the test subjects may be pre-tested to determine their sensitivity levels, with that data being used in connection with the present invention. Alternatively, the systems and methods of the present invention may also advantageously include determination of the test subjects' sensitivity levels by exposing the individuals to a sensitivity aerosol when they are not wearing a respirator.

If included in the present invention, it may be desirable, as a part of the fit test, that an automated aerosol generator system also be used to deliver a sensitivity aerosol to each of the test stations 20 occupied by a test subject, thereby exposing each of the test subjects to the sensitivity aerosol. Sensitivity testing is typically performed when the test subject is not wearing a respirator. The automated aerosol generator system used to deliver the sensitivity aerosol may be the same as that used to deliver the test aerosol, or a different aerosol generator system may be used. Also, the sensitivity aerosol and the test aerosol may be the same or different materials and/or concentrations.

It may be desirable to simultaneously deliver an initial selected amount of the sensitivity aerosol to each of the occupied tests stations 20. Alternatively, the delivery of sensitivity aerosol to the different test stations need not be simultaneous.

The method may also include receiving sensitivity feedback from the test subjects after exposure to the sensitivity aerosol. Sensitivity is often determined by exposing the test subjects at the occupied test stations 20 to increasing concentrations of the sensitivity aerosol. As a result, it may be desirable to prevent delivery of the sensitivity aerosol to a test station 20 occupied by a test subject after that test subject has indicated that he or she has detected the sensitivity aerosol. Preventing further delivery of the sensitivity aerosol may increase the comfort of the test subjects.

The sensitivity feedback may be used, in combination with the sensitivity aerosol delivery information, to set the concentration level of the test aerosol to which the test subject should be exposed during the later portion of the fit test. It may be desirable to store the sensitivity feedback received and the sensitivity aerosol delivery information in the database and correlate that information with the personal identification information of the test subject to assist in setting the test aerosol concentration levels.

Figure 2:
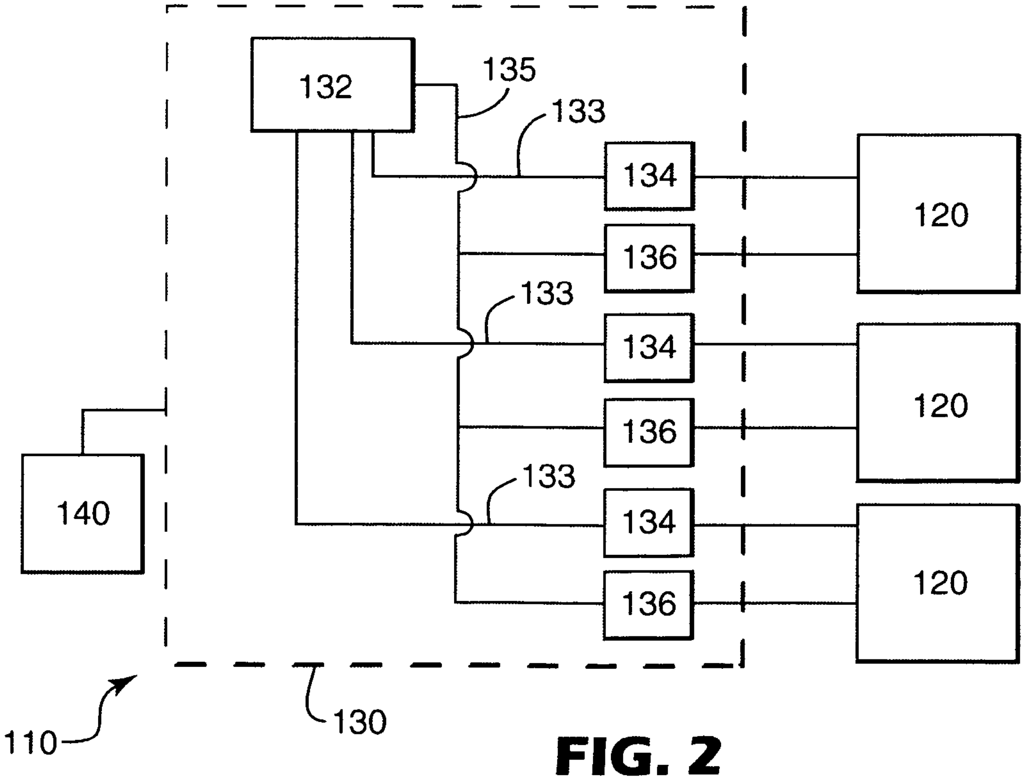
FIG. 2 is a schematic diagram of one aerosol generator system 130.

One illustrative embodiment of an alternative qualitative fit testing system 110 is depicted in more detail in FIG. 2. The system 110 includes multiple test stations 120 at which test subjects can be located during the fit testing process. The automated aerosol generator system 130 includes a set of independent test aerosol generators 134 used to generate test aerosol during fit testing. Each of the test aerosol generators 134 is in fluid communication with one of the test stations 120. In this configuration, the aerosol generator system 130 may be in "fluid communication" by providing a test aerosol generator 134 at each of the test stations 120. For example, each test aerosol generator 134 may feed its aerosol directly into the enclosed volume defined by the test station 120, without requiring any fluid conduits or other fluid delivery apparatus.

As used herein, the term "set of independent aerosol generators" (and variations thereof) means a set of aerosol generators that can deliver aerosol independent of each other. For example, one or more aerosol generators can be operated while others are not operating, each of the aerosol generators can deliver different amounts of aerosol at the same time, the aerosol generators can deliver different types of aerosols to the test stations, etc.

An optional set of independent sensitivity aerosol generators 136 is also depicted in FIG. 2, with each of the sensitivity aerosol generators 136 in fluid communication with one of the test stations 120. Either set of independent aerosol generators 134 or 136 may be replaced a central aerosol generator as depicted in connection with FIG. 1.

FIG. 2 also illustrates a controller 140 operably connected to the automated aerosol generator system 130 for controlling the delivery of aerosol to the test stations 120. The controller 140 may be provided in any suitable form, e.g., a hardwired control device or a data processing system, e.g., a personal computer or workstation that includes a processor, one or more display devices, one or more input devices, one or more data storage devices, and one or more printers or other output devices. In some instances, the controller may include a combination of one or more hardwired control devices and one or more data processing systems.

The automated aerosol generator system 130 and controller 140 can be located remote from each other and connected by any suitable technique, e.g., modem, hardwire connection, radio control, computer network connection, etc. Alternatively, the automated aerosol generator system 130 and controller 140 may be integrated into a single unit.

The test aerosol generators 134 and sensitivity aerosol generators 136 are operably connected to a power source 132 that provides the power necessary to operate the aerosol generators 134 and sensitivity aerosol generators 136. The power source 132 may, for example, be in the form of a pressurized gas source (e.g., air) if the aerosol generators 134 and optional sensitivity aerosol generators 136 are provided in the form of pressurized gas-powered nebulizers. Alternatively, the aerosol generators 134 and 136 may be, e.g., piezo-electric nebulizers, sonic nebulizers, etc. Regardless of their specific construction, the aerosol generators 134 and 136 may provide monodispersed aerosols or they may provide polydispersed aerosols as desired or required by the test protocol being conducted.

The power source 132 is depicted as being connected to each of the test aerosol generators 134 individually through lines 133. Each line 133 may include a power channel (e.g., fluid conduit for pressurized gas, cables for electrical power, etc.) and/or one or more signal lines. The signal line or line may operate a nebulizer, valve, etc. In this configuration of individual connections between power source 132 and test aerosol generators 134, it may be possible to operate each of the test aerosol generators 134 independently. As a result, two or more of the test aerosol generators 134 may be operated simultaneously to deliver the same or different selected amounts of test aerosol to their respective test stations 120. Alternatively, the test aerosol generators 134 may be actuated at different times and/or may deliver different selected amounts of the test aerosol to their respective test stations 120.

The sensitivity aerosol generators 136 are also connected to the power source 132, but through a common line 135 as opposed to individual lines 133. This configuration may be particularly amenable to simultaneous actuation of each of the sensitivity aerosol generators 136 to deliver sensitivity aerosol to each test station 120. It may, however, be possible to prevent actuation of one or more of the sensitivity aerosol generators 136 if, for example, a test subject at one of the test stations 120 has already indicated detection of the sensitivity aerosol at a lower concentration.

Figure 3:
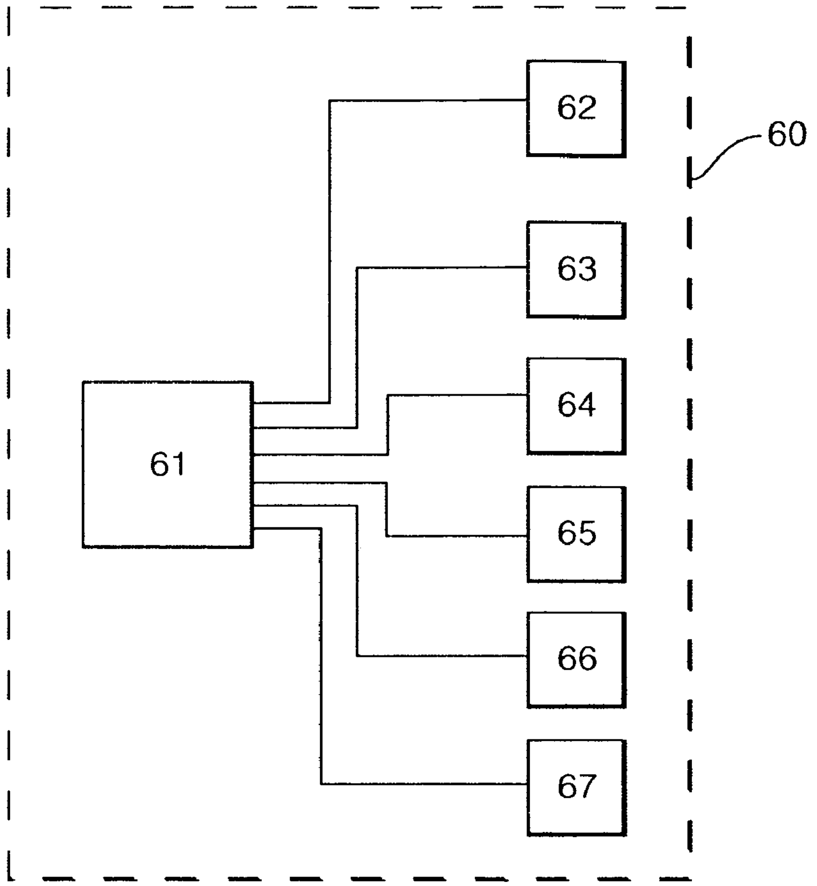
FIG. 3 is a schematic diagram of one data record 60 including a variety of fit testing information.

FIG. 3 is a schematic representation of a database 60 that may be used in connection with the present invention. The database 60 may be stored on any suitable device and/or in any suitable manner, e.g., on the hard drive of computer, a CD-ROM, tape, diskette, in volatile memory, etc. The database 60 may be stored locally at the site of the fit testing system and/or at a remote location. For example, the database 60 may be stored on a data storage device associated with the controllers described in connection with the systems of the present invention.

The database 60 may include a variety of information including, e.g., personal identification information of a test subject 61, sensitivity feedback 62, sensitivity delivery information 63, test feedback 64, test aerosol delivery information 65, at least one captured image 66, and activity feedback 67. The database 60 may include other types of information as well. In another alternative, the database may store, e.g., only a single piece of information regarding sensitivity of the test subject (as opposed to both sensitivity feedback 62 and sensitivity aerosol delivery information 63). It is preferred, but not required, that the information related to a specific test subject be correlated with the personal identification information 61 of that test subject in the database 60.

The database 60 may serve a variety of purposes. For example, it may be used to improve respirator design by allowing a manufacturer to identify respirators that generate larger numbers of fit test failures, it may be used to monitor compliance with fit testing requirements, etc.

Figure 4:
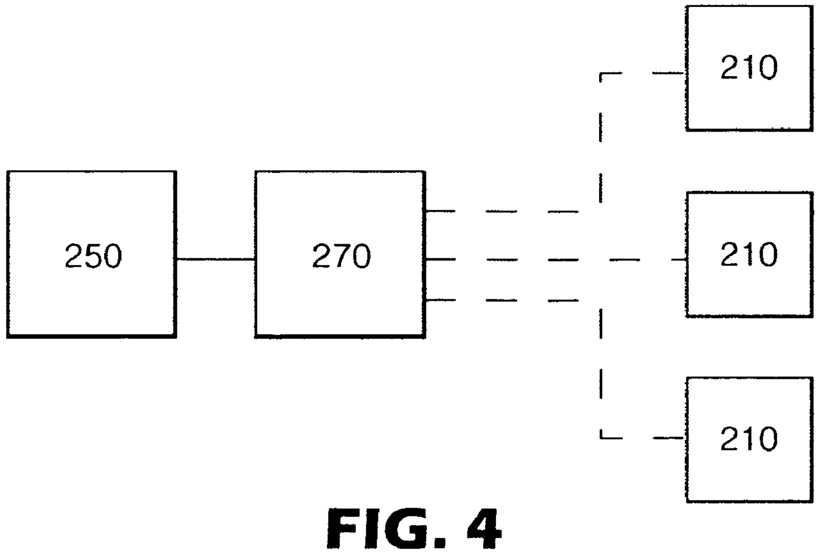
FIG. 4 is a schematic diagram of one test administrator 150 using multiple fit testing systems 110.

The systems and methods of the present invention provide opportunities in the administration of respirator fit testing programs not previously available. FIG. 4 is a schematic diagram depicting a centralized test administrator 250 operating a centralized fit test controller 270 in communication with multiple automated respirator fit testing systems 210.

The controller 270 may be provided in any suitable form, e.g., a hardwired control device or a data processing system, e.g., a personal computer or workstation that includes a processor, one or more display devices, one or more input devices, one or more data storage devices, and one or more printers or other output devices. In some instances, the controller 270 may include a combination of one or more hardwired control devices and one or more data processing systems.

The centralized fit test administrator 250 and associated controller 270 may operate the different automated respirator fit testing systems 210 simultaneously or at different times. The centralized fit test administrator 250, and central controller 270 may be located at sites remote from each other and the automated respirator fit testing systems 210. As used herein, "operate" (and variations thereof), means that the administrator 250 controls the remote automated respirator fit testing systems 210 in a manner that allows the administrator 250 to initiate, monitor, and/or terminate respirator fit tests being conducted by the systems 210 at the remote sites.

The test administrator 250 and controller 270 may be linked to the fit testing systems 210 by any suitable technique that offers the required level of data transmission, e.g., modem, hardwire connection, radio control, computer network connection, etc. It may further be preferred that the test administrator 250 and controller 270 be capable of conducting respirator fit tests at two or more of the fit testing systems 210 at the same time.

The automated respirator fit testing systems 210 themselves may include two or more tests stations and be capable of simultaneously fit testing multiple individuals. Alternatively, one or more of the respirator fit testing systems 210 may be supplied with only one test station. Regardless of whether the fit testing systems 210 are capable of processing only one test subject at a time or more than one test subject simultaneously, the opportunity for remote administration of respirator fit tests may offer the advantages of increased access to test administrators and potentially lower cost fit testing.

As part of the remote administration of respirator fit tests, operation of the automated respirator fit testing systems may include receiving test feedback at the site of the administrator 250 and/or central controller 270 from a test subject at one of the fit testing systems 210 after exposure to the test aerosol. Alternatively, the test feedback may be received locally at the site of the automated respirator fit testing system 210 at which the test is being conducted.

Regardless of where received, the test feedback may be stored in a database as discussed above. The database may be located in a device that forms a part of the respirator fit testing system 210 at the testing site, in a device that forms a part of the central controller 270, in a device at the location of the administrator 250, and/or in some other location. Remote administration may also involve storing information regarding the test aerosol delivery during fit testing in the database.

Remote administration of a respirator test may also include monitoring the test stations at which respirator fit tests are being performed. In addition to monitoring, remote administration may also include capturing at least one image during the monitoring. That captured image (or images) may also be stored in one or more databases as discussed above.

Prompting of test subjects at the different sites of the test systems may also be a part of remote respirator fit test administration. For example, a test administrator 250 may prompt the subjects to perform specified activities as a part of the fit tests, the central controller 270 may generate prompts once the test has been initiated, or the local automated respirator fit testing system 210 may generate the prompts. In some instances, it may be desirable to allow the prompts to originate from more than one location. For example, it may be desirable to deliver the prompts from the local test system 210, but to allow the administrator 250 to deliver additional prompts as deemed necessary. Remote test administration may also include receiving activity feedback from the test subjects indicating completion of the specified activities and in a manner similar to receipt (and optional storage) of test feedback described above.

The preceding specific embodiments are illustrative of the practice of the invention. This invention may be suitably practiced in the absence of any element or item not specifically described in this document. The complete disclosures of all patents, patent applications, and publications are incorporated into this document by reference as if individually incorporated in total.

Various modifications and alterations of this invention will become apparent to those skilled in the art without departing from the scope of this invention, and it should be understood that this invention is not to be unduly limited to illustrative embodiments set forth herein, but is to be controlled by the limitations set forth in the claims and any equivalents to those limitations.

What is claimed is:

1. A method of qualitative respirator fit testing, the method comprising:

providing an automated qualitative respirator fit testing system that comprises a plurality of test stations and an automated aerosol generator system in fluid communication with each of the test stations, wherein the automated aerosol generator system comprises a set of independent aerosol generators, with at least one of the independent aerosol generators in fluid communication with each of the test stations;

locating at least one test subject at one test station of the plurality of test stations; and conducting a qualitative fit test on each test subject located at one of the test stations, wherein the qualitative fit test conducted at each of the test stations comprises:

delivering a test aerosol to the test station using the automated aerosol generator system after locating a respirator on the test subject, wherein the test subject is exposed to the test aerosol; and receiving test feedback from the test subject at the test station after exposure to the test aerosol.

2. The method of claim 1, further comprising locating two or more test subjects at the plurality of test stations and conducting a qualitative fit test on each of the two or more test subjects simultaneously.

3. The method of claim 2, wherein delivering the test aerosol further comprises simultaneous delivery of the test aerosol to the two or more test subjects.

4. The method of claim 1, where in providing the test aerosol further comprises delivering a selected amount of the test aerosol to each of the test subjects at predetermined intervals using the aerosol generator system.

5. The method of claim 4, further comprising delivering the selected amount of the test aerosol to each of the test subjects simultaneously.

6. The method of claim 4, further comprising delivering different selected amounts of the test aerosol to at least two of the test stations.

7. The method of claim 1, further comprising storing the test feedback in a database.

8. The method of claim 1, further comprising storing information regarding the test aerosol delivery to each of the test subjects in a database.

9. The method of claim 1, further comprising monitoring each of the test stations during exposure of the test subjects to the test aerosol.

10. The method of claim 1, further comprising prompting the test subjects at each of the test stations to perform specified activities during exposure of the test subject to the test aerosol.

11. The method of claim 10, further comprising simultaneous prompting of at least two test subjects to perform the specified activities.

12. The method of claim 10, further comprising receiving activity feedback from each of the test subjects indicating completion of the specified activities.

13. The method of claim 1, comprising:

capturing at least one image of at least one test subject at one of the test stations during exposure of the test subject to the test aerosol; and storing the at least one image in a database.

14. A method of qualitative respirator fit testing, the method comprising:

providing an automated qualitative respirator fit testing system that comprises a plurality of test stations and an automated aerosol generator system in fluid communication with each of the test stations;

locating at least one test subject at one test station of the plurality of test stations; and conducting a qualitative fit test on each test subject located at one of the test stations, wherein the qualitative fit test conducted at each of the test stations comprises:

delivering a test aerosol to the test station using the automated aerosol generator system after locating a respirator on the test subject, wherein the test subject is exposed to the test aerosol;

receiving test feedback from the test subject at the test station after exposure to the test aerosol;

monitoring each of the test stations during exposure of the test subject to the test aerosol to each of the test stations;

capturing at least one image of the test station during the monitoring; and storing the at least one image in a database.

15. A method of qualitative respirator fit testing, the method comprising:

providing an automated qualitative respirator fit testing system that comprises a plurality of test stations and an automated aerosol generator system in fluid communication with each of the test stations;

locating at least one test subject at one test station of the plurality of test stations; and conducting a qualitative fit test on each test subject located at one of the test stations, wherein the qualitative fit test conducted at each of the test stations comprises:

delivering a test aerosol to the test station using the automated aerosol generator system after locating a respirator on the test subject, wherein the test subject is exposed to the test aerosol;

receiving test feedback from the test subject at the test station after exposure to the test aerosol;

delivering sensitivity aerosol to the test station using the automated aerosol generator system, wherein the test subject is exposed to the sensitivity aerosol; and receiving sensitivity feedback from the test subject at the test station after exposure to the sensitivity aerosol.

16. The method of claim 15, further comprising simultaneous delivery of an initial selected amount of the sensitivity aerosol to each of at least two test subjects.

17. The method of claim 15, further comprising preventing delivery of the sensitivity aerosol to at least one test subject after receiving sensitivity feedback from the test subject indicating detection of the sensitivity aerosol by the test subject after delivering the initial selected amount of the sensitivity aerosol.

18. The method of claim 15, further comprising storing the sensitivity feedback in a database.

19. The method of claim 15, further comprising storing information regarding the sensitivity aerosol delivery to each of the test subjects in the database.

20. A qualitative respirator fit testing system comprising:

a plurality of test stations; and an automated aerosol generator system in fluid communication with each of the test stations, wherein the automated aerosol generator system comprises a set of independent aerosol generators, wherein at least one of the independent aerosol generators is in fluid communication with each of the test stations.

21. The system of claim 20, wherein each of the aerosol generators comprises a nebulizer.

22. The system of claim 20, wherein each of the test stations comprises a respirator fit testing hood.

23. A method of remote automated respirator fit testing comprising:

providing an automated respirator fit testing system at a first location, wherein the automated respirator fit testing system comprises at least one test station and an automated aerosol generator system in fluid communication with each of the at least one test stations;

locating at least one test subject wearing a respirator at the test station of the respirator fit testing system at the first location;

operating the automated respirator fit testing system from a remote location to perform a respirator fit test on the at least one test subject by delivering a test aerosol to the at least one test station using the automated aerosol generator system, wherein the at least one test subject is exposed to the test aerosol;

monitoring the at least one test station while performing the respirator fit test;

capturing at least one image of the at least one test station during the monitoring; and storing the at least one image in a database.

24. The method of claim 23, wherein operating the respirator fit testing system comprises receiving test feedback at the remote location from the test subject at the first location after exposure to the test aerosol.

25. The method of claim 24, further comprising storing the test feedback in a database.

26. The method of claim 23, further comprising storing information regarding the test aerosol delivery in a database.

27. The method of claim 23, further comprising prompting the at least one test subject to perform specified activities while performing the respirator fit test.

28. The method of claim 23, further comprising receiving activity feedback from the at least one test subject indicating completion of specified activities while performing the respirator fit test.

29. The method of claim 23, further comprising simultaneous prompting of at least two test subjects to perform specified activities.

30. The method of claim 23, further comprising:

providing a second automated respirator fit testing system at a second location remote from the first location, wherein the second automated respirator fit testing system comprises at least one test station and an automated aerosol generator system in fluid communication with each of the at least one test stations;

locating at least one test subject wearing a respirator at the test station of the second automated respirator fit testing system at the second location; and operating the first and second automated respirator fit testing systems from the remote location to perform a respirator fit test on the at least one test subject located at each of the first and second automated respirator fit testing systems, wherein each respirator fit test comprises delivering a test aerosol to the at least one test station using the automated aerosol generator system, wherein the at least one test subject is exposed to the test aerosol.

31. The method of claim 30, further comprising conducting respirator fit tests using the first and second automated respirator fit testing systems at the same time.

32. A method of qualitative respirator fit testing, the method comprising:

providing an automated qualitative respirator fit testing system that comprises a plurality of test stations and an automated aerosol generator system in fluid communication with each of the test stations;

locating at least one test subject at one test station of the plurality of test stations; and conducting a qualitative fit test on each test subject located at one of the test stations, wherein the qualitative fit test conducted at each of the test stations comprises:

delivering different selected amounts of test aerosol to at least two of the test stations using the automated aerosol generator system after locating a respirator on test subjects at the at least two of the test stations, wherein the test subjects are exposed to the different selected amounts of test aerosol at the same time; and receiving test feedback from the test subject at the test station after exposure to the test aerosol.

33. The method of claim 32, wherein each test station of the plurality of test stations comprises an independent environment wherein test aerosol delivered to one test station of the plurality of test stations cannot be communicated to the other test stations of the plurality of test stations.

34. A method of qualitative respirator fit testing, the method comprising:

providing an automated qualitative respirator fit testing system that comprises a plurality of test stations and an automated aerosol generator system in fluid communication with each of the test stations, wherein each test station of the plurality of test stations comprises an independent environment wherein test aerosol delivered to one test station of the plurality of test stations cannot be communicated to the other test stations of the plurality of test stations;

locating at least one test subject at one test station of the plurality of test stations; and conducting a qualitative fit test on each test subject located at one of the test stations, wherein the qualitative fit test conducted at each of the test stations comprises:

delivering a test aerosol to the test station using the automated aerosol generator system after locating a respirator on the test subject, wherein the test subject is exposed to the test aerosol; and receiving test feedback from the test subject at the test station after exposure to the test aerosol.

35. A method of qualitative respirator fit testing, the method comprising:

providing an automated qualitative respirator fit testing system that comprises a plurality of test stations and an automated aerosol generator system in fluid communication with each of the test stations, wherein each test station of the plurality of test stations comprises an independent environment wherein test aerosol delivered to one test station of the plurality of test stations cannot be communicated to the other test stations of the plurality of test stations;

locating at least one test subject at one test station of the plurality of test stations; and conducting a qualitative fit test on each test subject located at one of the test stations, wherein the qualitative fit test conducted at each of the test stations comprises:

delivering a test aerosol to the test station using the automated aerosol generator system after locating a respirator on the test subject, wherein the test subject is exposed to the test aerosol;

receiving test feedback from the test subject at the test station after exposure to the test aerosol;

delivering sensitivity aerosol to the test station using the automated aerosol generator system, wherein the test subject is exposed to the sensitivity aerosol; and receiving sensitivity feedback from the test subject at the test station after exposure to the sensitivity aerosol.

36. A qualitative respirator fit testing system comprising:

a plurality of test stations; and an automated aerosol generator system in fluid communication with each of the test stations;

wherein each test station of the plurality of test stations comprises an independent environment wherein test aerosol delivered to one test station of the plurality of test stations cannot be communicated to the other test stations of the plurality of test stations.

37. A qualitative respirator fit testing system comprising:

a plurality of test stations, wherein each of the test stations comprises a respirator fit testing hood; and an automated aerosol generator system in fluid communication with each of the test stations;

wherein the respirator fit testing hood at each test station of the plurality of test stations comprises an independent environment wherein test aerosol delivered to one test station of the plurality of test stations cannot be communicated to the other test stations of the plurality of test stations.

38. A method of remote automated respirator fit testing comprising:

providing an automated respirator fit testing system at a first location, wherein the automated respirator fit testing system comprises at least one test station and an automated aerosol generator system in fluid communication with each of the at least one test stations;

locating at least one test subject wearing a respirator at the test station of the respirator fit testing system at the first location;

operating the automated respirator fit testing system from a remote location to perform a respirator fit test on the at least one test subject by delivering a test aerosol to the at least one test station using the automated aerosol generator system wherein the at least one test subject is exposed to the test aerosol;

providing a second automated respirator fit testing system at a second location remote from the first location, wherein the second automated respirator fit testing system comprises at least one test station and an automated aerosol generator system in fluid communication with each of the at least one test stations;

locating at least one test subject wearing a respirator at the test station of the second automated respirator fit testing system at the second location; and operating the first and second automated respirator fit testing systems from the remote location to perform a respirator fit test on the at least one test subject located at each of the first and second automated respirator fit testing systems, wherein each respirator fit test comprises delivering a test aerosol to the at least one test station using the automated aerosol generator system, wherein the at least one test subject is exposed to the test aerosol, and wherein each test station comprises an independent environment wherein test aerosol delivered to one test station cannot be communicated to another test station.

39. A method of qualitative respirator fit testing, the method comprising:

providing an automated qualitative respirator fit testing system that comprises a plurality of test stations and an automated aerosol generator system in fluid communication with each of the test stations, wherein each test station of the plurality of test stations comprises an independent environment wherein test aerosol delivered to one test station of the plurality of test stations cannot be communicated to the other test stations of the plurality of test stations;

locating at least one test subject at one test station of the plurality of test stations; and conducting a qualitative fit test on each test subject located at one of the test stations, wherein the qualitative fit test conducted at each of the test stations comprises:

delivering a repeatable, selected amount of test aerosol to the test station using the automated aerosol generator system after locating a respirator on the test subject, wherein the test subject is exposed to the test aerosol; and receiving test feedback from the test subject at the test station after exposure to the test aerosol.

* * * * *

UNITED STATES PATENT AND TRADEMARK OFFICE

CERTIFICATE OF CORRECTION

PATENT NO. : 6,955,170 B1 
DATED : October 18, 2005
INVENTOR(S) : Mullins, Haskell E.

It is certified that error appears in the above-identified patent and that said Letters Patent is hereby corrected as shown below:

<u>Title page,</u>
Item [56], References Cited, OTHER PUBLICATIONS,
"Prototype…" reference, after "Burstroem" insert -- et al. --.

<u>Column 12,</u>
Line 14, delete "where in" and insert -- wherein --.

<u>Column 16,</u>
Line 31, after "system" insert -- , --.

Signed and Sealed this

Thirty-first Day of January, 2006

JON W. DUDAS
*Director of the United States Patent and Trademark Office*